United States Patent
Hokamura et al.

(10) Patent No.: US 8,649,013 B2
(45) Date of Patent: Feb. 11, 2014

(54) PROBE FOR GAS ANALYSIS

(75) Inventors: Shigeyuki Hokamura, Kyoto (JP); Toshikazu Ohnishi, Kyoto (JP); Takuya Ido, Kyoto (JP)

(73) Assignee: Horiba, Ltd, Kyoto (JP)

( * ) Notice: Subject to any disclaimer, the term of this patent is extended or adjusted under 35 U.S.C. 154(b) by 9 days.

(21) Appl. No.: 13/198,174

(22) Filed: Aug. 4, 2011

(65) Prior Publication Data

US 2012/0033219 A1  Feb. 9, 2012

(30) Foreign Application Priority Data

Aug. 4, 2010 (JP) .................. 2010-175733

(51) Int. Cl.
   *G01N 21/00* (2006.01)
(52) U.S. Cl.
   USPC ......................................... 356/438; 356/432

(58) Field of Classification Search
   USPC ................ 356/432–442, 244, 246, 337–343; 250/343, 336.1, 338.1, 373–375
   See application file for complete search history.

(56) References Cited

U.S. PATENT DOCUMENTS 4,560,873 A * 12/1985 McGowan et al. ...... 250/339.09
5,781,306 A    7/1998 Hartig et al.

\* cited by examiner

*Primary Examiner* — Tri T Ton
(74) *Attorney, Agent, or Firm* — Brooks Kushman P.C.

(57) ABSTRACT

A probe for gas analysis is provided in a pipe through which sample gas flows. The probe includes a tubular member and one or more sample gas inflow portions. The tubular member is disposed to cross a flow of the sample gas, and includes a measurement field to which the sample gas is introduced. The one or more sample gas inflow portions are provided in the tubular member. The sample gas flows around, and flows into the measurement field through the one or more sample gas inflow portions.

9 Claims, 11 Drawing Sheets

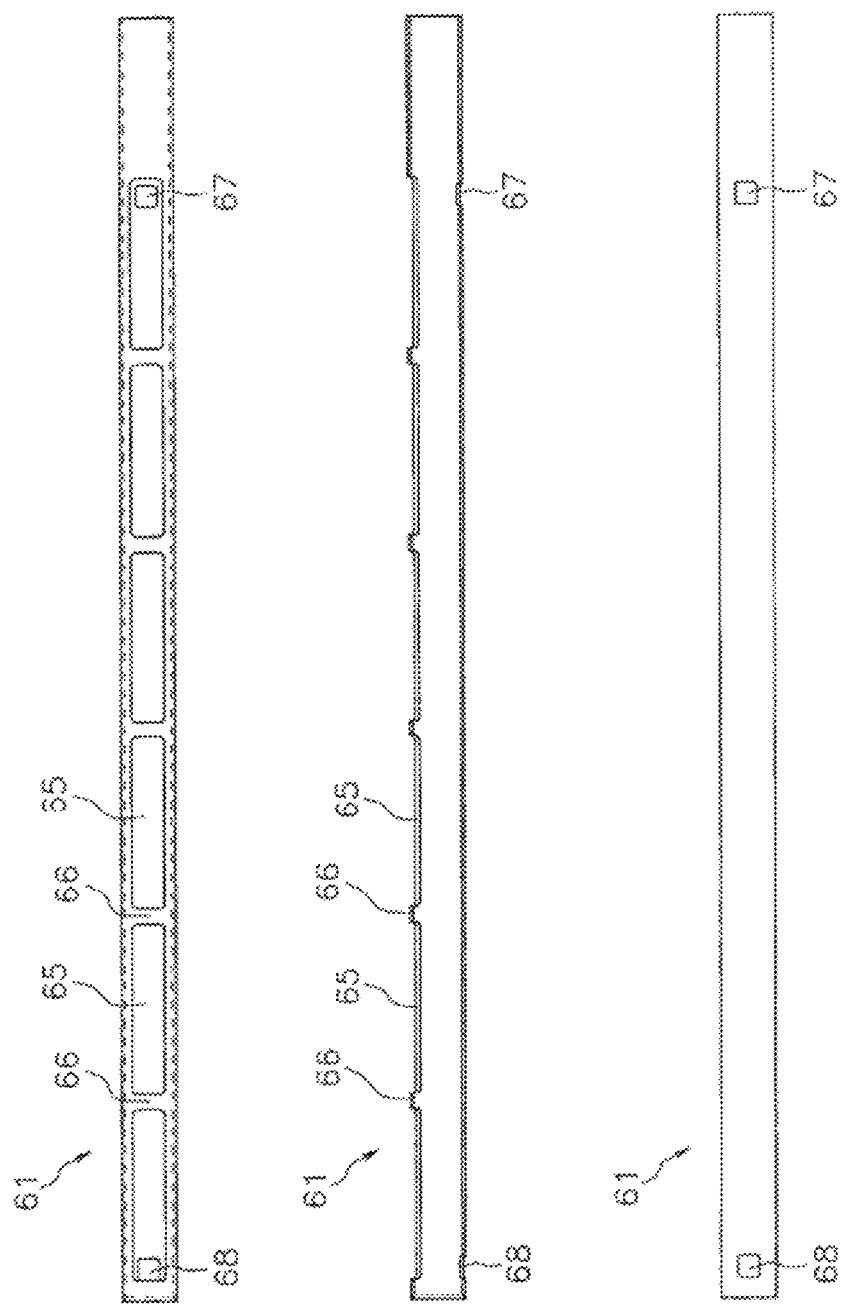

PROBE FOR GAS ANALYSIS

CROSS-REFERENCE TO RELATED APPLICATIONS

This application claims priority under 35 U.S.C. §119 to Japanese Patent Application No. 2010-175733 filed on Aug. 4, 2010. The entire disclosure of Japanese Patent Application No. 2010-175733 is hereby incorporated herein by reference.

BACKGROUND

1. Technical Field

The present disclosure is related to gas analysis probes as probes for gas analysis.

2. Background Information

Conventionally, exhaust combustion gas exhausted from a boiler that combusts coal or heavy oil includes components such as NOx, SOx, SO2, CO2, and CO. Constantly, the component amount is analyzed by a gas analyzer, and the result of analysis is used for control such as denitrification and desulfurization, as well as for ecological monitoring. The gas analyzer may be an open-path type and a probe-type.

The above-mentioned probe-type gas analyzer includes a tubular probe for gas analysis, which is disposed perpendicular to a pipe through which exhaust combustion gas flows, as disclosed in the specification of U.S. Pat. No. 5,781,306. The above-described probe for gas analysis will be explained hereinafter.

FIG. 10 is a schematic side view of a conventional (prior art) probe for gas analysis. A probe 200 shown in FIG. 10 has the shape of a tube, and is arranged perpendicular to a pipe 202 (e.g., gas flue). The probe 200 is formed with an opening 203A and an opening 203B respectively on an upstream side and a downstream side with respect to a flow direction of sample gas S (e.g., exhaust combustion gas). The sample gas S flowing in the pipe 202 flows into the probe 200 through the opening 203A, and flows out through the opening 203B. Accordingly, the probe 200 is filled with the sample gas S. Then, a measuring light for measuring objects is passed through a measurement field (e.g., measurement cells) formed in the probe 200, and the attenuation amount of the measuring light is used for quantitative determination of the measured objects.

However, according to the above-described probe, the opening is formed on the upstream side with respect to the flow direction of exhaust combustion gas, so the dust along with the gas component in the exhaust combustion gas flows into the probe. Particularly, when the amount of the dust is large, in the measurement cell, the dust causes absorption and scattering of the measuring light, resulting in the attenuation of the measuring light. Accordingly, the quantity of light for measurement likely cannot be obtained. In other words, the measurement accuracy may be reduced.

SUMMARY

Embodiments according to the present disclosure were conceived in light of the above-described problem to provide a probe for gas analysis into which the dust is prevented from entering, thereby ensuring proper quantity of the measuring light passing through the probe, and achieving a gas analysis with high measurement accuracy.

A gas analysis probe or a probe for gas analysis according to an aspect of the present invention is a device for, or to be used or disposed in, a pipe through which sample gas flows. The probe includes a tubular member and one or more sample gas inflow portions. The tubular member is disposed to cross the flow of the sample gas, and includes a measurement field to which the sample gas is introduced. The one or more sample gas inflow portions are provided at the tubular member. Some of the sample gas flows around and flows into the measurement field through the one or more sample gas inflow portions.

These and other features, aspects, and advantages of the present disclosure will become apparent to those skilled in the art from the following detailed description, which, taken in conjunction with the annexed drawings, discloses preferred embodiments of the present invention.

BRIEF DESCRIPTION OF THE DRAWINGS

Referring now to the attached drawings which form a part of this original disclosure:

FIG. 3A is a plan view of the tubular member shown in FIG. 2, FIG. 3B is a transverse sectional view of the tubular member, and FIG. 3C is a rear view of the tubular member;

DETAILED DESCRIPTION OF THE PREFERRED EMBODIMENTS

Selected embodiments of the present disclosure will now be explained with reference to the drawings. It will be apparent to those skilled in the art from this disclosure that the following descriptions of the embodiments are provided as examples only and are not meant to limit the appended claims and their equivalents. Various features illustrated and/or described with respect to a particular embodiment may be combined with features illustrated and/or described with respect to one or more other embodiments to produce embodiments of the present disclosure that may not be explicitly illustrated or described. The combinations of features explicitly illustrated and/or described provide representative embodiments for typical applications. However, various combinations and modifications of the features consistent with the teachings of the present disclosure may be desired for particular applications or implementations.

1. First Embodiment

Figure 1:
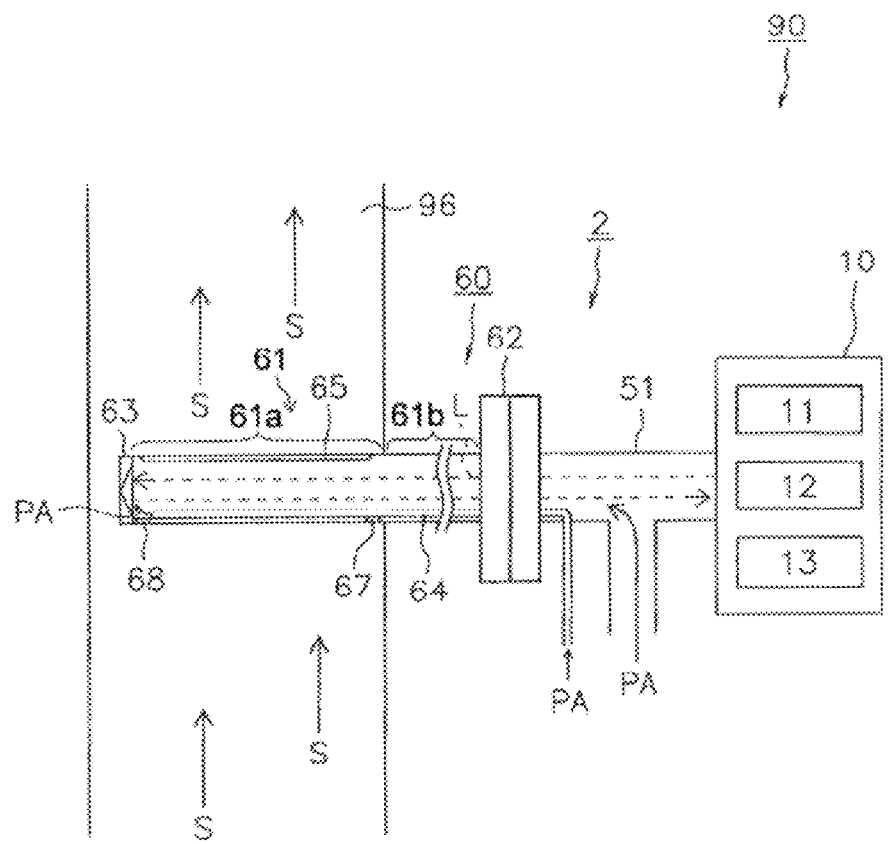
FIG. 1 is a schematic diagram of an optical analyzer provided with a probe for gas analysis according to an embodiment of the present invention.
Figure 2:
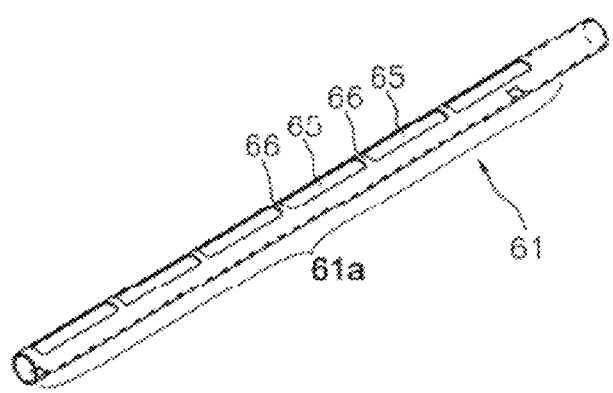
FIG. 2 is a perspective view of a tubular member of the probe for gas analysis shown in FIG. 1.

Hereinafter, one embodiment according to the present disclosure will be explained with the accompanying drawings. FIG. 1 is a block diagram for illustrating an optical analyzer including a probe for gas analysis according to an embodiment of the present invention. FIG. 2 is a perspective view of a tubular member of the probe shown in FIG. 1. FIG. 3A is a plan view of the tubular member shown in FIG. 2, FIG. 3B is a transverse sectional view of the tubular member, and FIG. 3C is a rear view of the tubular member.

An optical analyzer 90 according to the embodiment includes a measuring device 10 and an analysis unit 2. The measuring device 10 is a typical one including a light source 11 (e.g., laser or LED) for emitting a measurement light, a light detecting unit 12 (e.g., a photodiode), and a control unit 13. The control unit 13 controls actions of the light source 11 and the light detecting unit 12, and calculates the density of the analyzed object based on signals the light detecting unit 12 receives. The control unit 13 may be composed of analog circuits or digital circuits such as a CPU.

The analysis unit 2 includes a probe for gas analysis 60 and a hollow optical guiding tube 51 for guiding the light emitted from the light source 11 into the probe 60. The probe 60 mainly consists of a tubular member 61. The probe 60 further includes a flange 62 provided on one end of the tubular member 61. The optical guiding tube 51 and the probe 60 are connected to each other through the flange 62.

The tubular member 61 is disposed in a pipe 96 through which sample gas S flows such that the tubular member 61 is generally perpendicular to the flow of the sample gas S. The tubular member 61 includes a first part 61a disposed in the pipe 96, and a second part 61b disposed out of the pipe 96. The first part 61a includes a measurement field 69 (later described) therein. The tubular member 61 is formed with openings 65 as a sample gas inflow portion, i.e., along the first part 61a. The openings 65 are formed only on a downstream side of the first part 61a of the tubular member 61, with respect to a flow direction of the sample gas S. The openings 65 are formed along an entire length of the measurement field 69 (refer to FIG. 5), which will be called "effective cell length" hereinafter. The openings 65 enable the sampling of the sample gas S. The openings 65 are partitioned by ribs 66, with the ribs 66 being positioned with predetermined gaps in between, as shown in FIG. 2 and FIG. 3, thereby improving the strength of the tubular member 61.

The tubular member 61 may have a shape or form of an elongated and/or linear tube with a symmetry axis along its extension and defining a longitudinal direction as its extension direction.

As explained above, the openings 65 include a plurality of apertures formed along a longitudinal direction of the tubular member 61.

While the tubular member 61 is disposed in the piping 96 such that the tubular member 61 is generally or substantially perpendicular to the flow of the sample gas S according to the present embodiment, the tubular member may be disposed in a different way. The tubular member only has to be provided in the pipe such that the tubular member crosses the flow of the sample gas. For example, the probe may be disposed obliquely such that one end of the tubular member opposite from the flange is located downstream of the flange.

The tubular member 61 is provided with a mirror 63 on the opposite end from the flange, and the mirror 63 reflects the light emitted from the light source 11 toward the light detecting unit 12. Then, the light detecting unit 12 measures light intensity of the reflected light, so that the object to be measured in the sample gas S is measured based on attenuation amount of the light.

The probe for gas analysis 60 according to the present embodiment reduces the dust in the sample gas entering into the tubular member 61, so that it is possible to ensure proper quantity of the light (measuring light) passing through the inside of the tubular member 61. The probe 60 will be described in detail hereinafter.

Figure 4A:
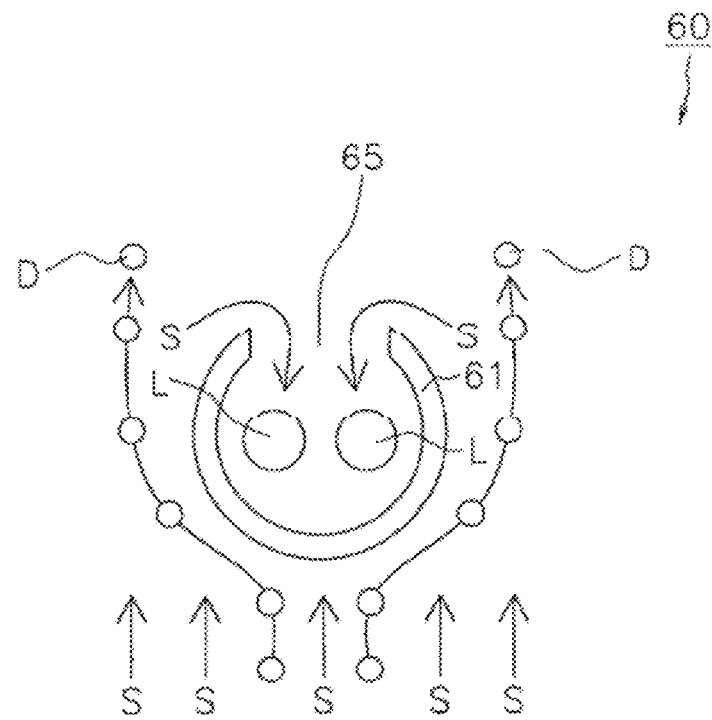
FIG. 4A and FIG. 4B are longitudinal sectional views of the probe for gas analysis shown in FIG. 1.
Figure 4B:
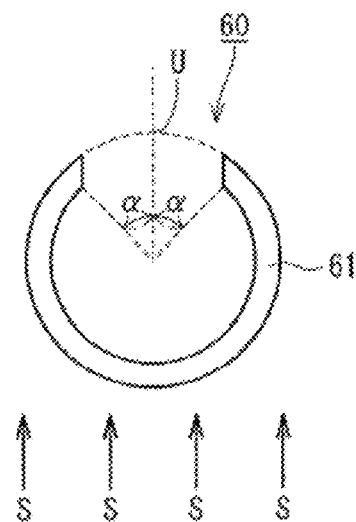

FIG. 4A is a longitudinal sectional view of the probe for gas analysis shown in FIG. 1. The tubular member 61 of the probe 60 is formed with the openings 65 only on the downstream side, along the entire effective cell length. That is, the upstream side of the tubular member 61 is not formed with the openings. Accordingly, the dust D in the sample gas S does not enter the tubular member 61 from the upstream side. The sample gas S flows around the probe 60 and enters the tubular member 61 through the openings 65. In contrast, the dust D in the sample gas S continues to move in the direction of movement (downstream direction) due to the law of inertia because the dust D has a certain degree of mass. Accordingly, the dust D does not tend to flow around the probe 60 nor flows into the probe 60 through the openings 65. It should be noted that taking a sample from the downstream side means, when the tubular member 61 is seen from the side and divided along the circumferential direction as shown in FIG. 4B, taking the sample gas from positions where an angle α (alpha) from the most downstream point U is less than 90 degrees, preferably less than 60 degrees. The angle α is therefore an opening angle for a respective opening or aperture 65, in particular in relation the tubular member's 61 symmetry axis or axis of longitudinal extension.

As described above, in the probe 60 according to the present embodiment, it is possible to have the sample gas S flow into the probe through the downstream-side openings 65 and to prevent the dust D from flowing into the probe 60. As a result, it is possible to ensure proper quantity of the measuring light passing through the probe 60. In addition, since it is possible to reduce the inflow of the dust D into the probe 60, the accumulation of the dust D can be decreased, thereby minimizing the need for periodic cleanings.

Furthermore, as shown in FIG. 1, in the optical analyzer 90, the purge air PA is introduced from the optical guiding tube 51 toward the probe 60. Accordingly, it is possible to reduce the contamination of the light source 11 and the light detecting unit 12 due to the dust flowing into the probe with the sample gas S. In addition, a purge air outflow tube 64 is provided within the tubular member 61 for guiding the purge air PA from the flange 62 toward the mirror 63. Accordingly, it is possible to prevent the contamination of the mirror 63 due to the dust flowing into the probe with the sample gas S.

However, if the above configuration is employed, the purge air PA may flow toward the center of the first part 61a of the tubular member 61, and may decrease the density of the sample gas S, thereby making it impossible to measure the sample gas S accurately. Therefore, in order to solve the problem, in the probe for gas analysis 60, a hole 67 is formed on the upstream side near the end towards the flange 62 (see FIG. 1 and FIG. 3), and a hole 68 is formed on the upstream side near the other end (i.e., the end towards the mirror 63), as shown in FIG. 1 and FIG. 3, so that it is possible to prevent the purge air PA from progressing further inward, i.e., toward the center of a measurement field (later described). It should be noticed that the hole 67 and the hole 68 are formed at both ends of the first part 61a of the tubular member 61. The structure and the function thereof will be described in detail hereinafter.

Figure 5:
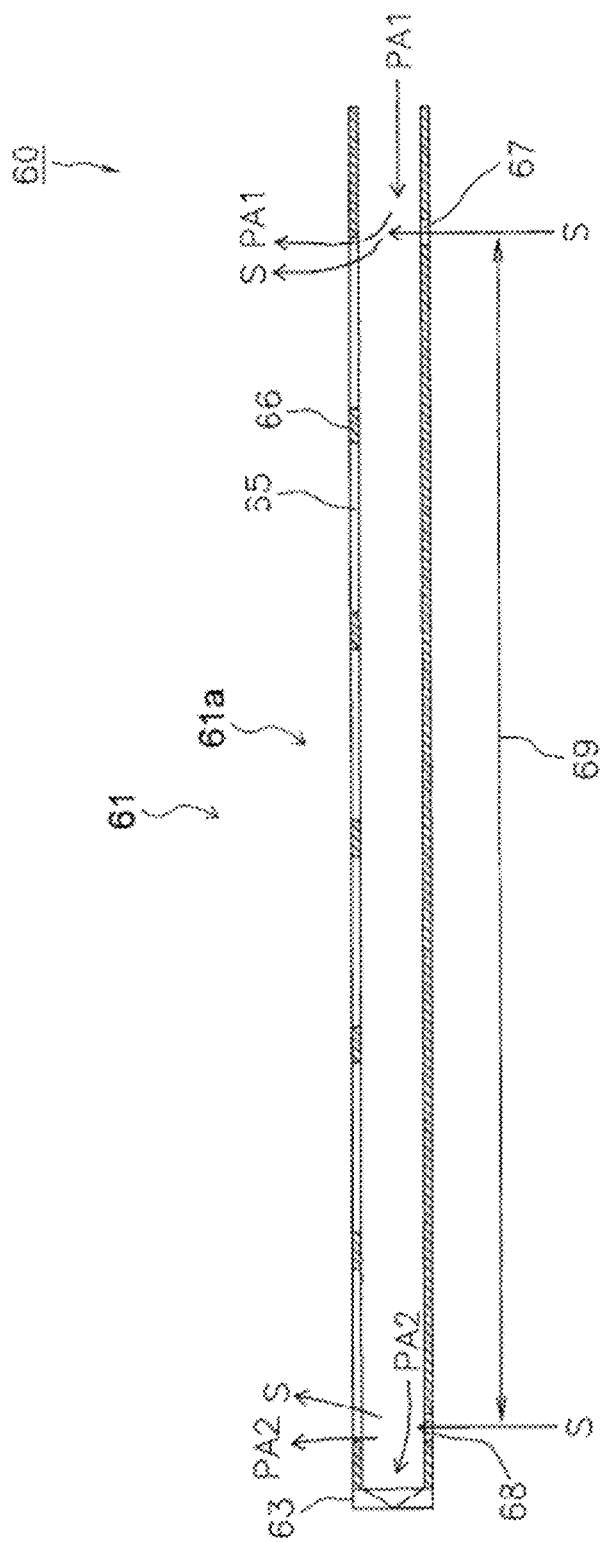
FIG. 5 is a transverse sectional view of the probe for gas analysis shown in FIG. 1.
Figure 6A:
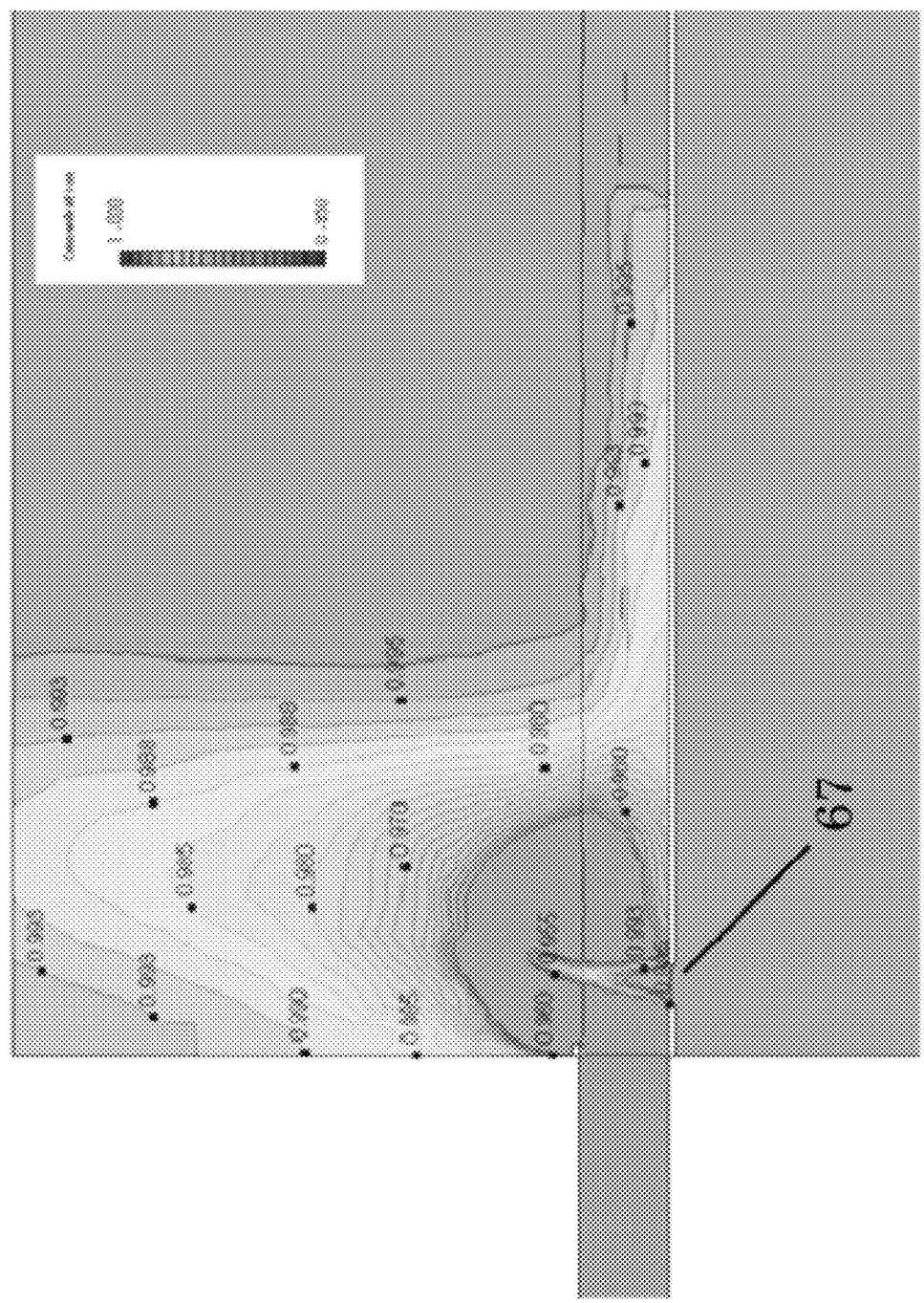
FIG. 6A through FIG. 6D are views of simulation results of the purge air blocking effect.
Figure 6B:
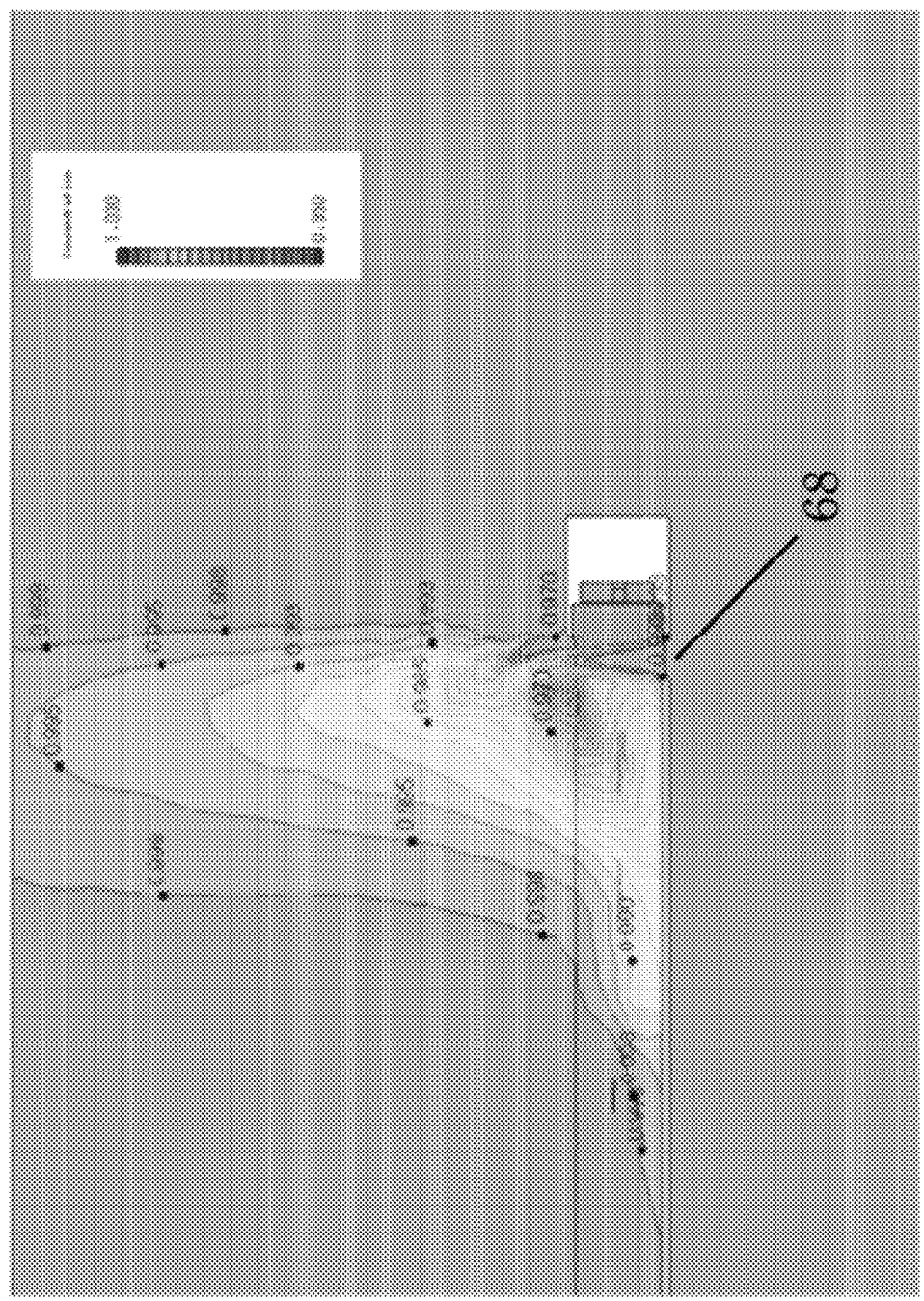
Figure 6C:
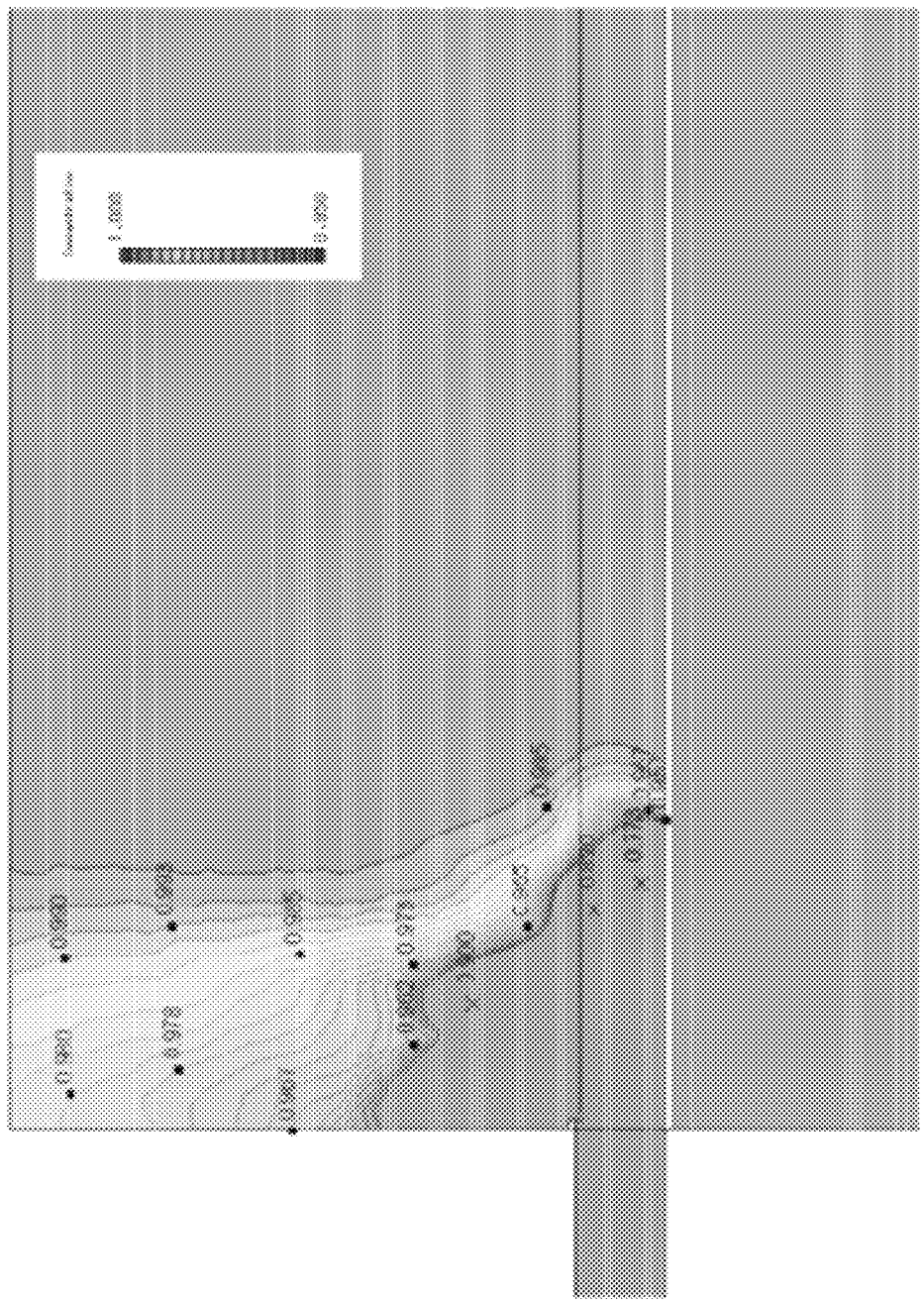
Figure 6D:
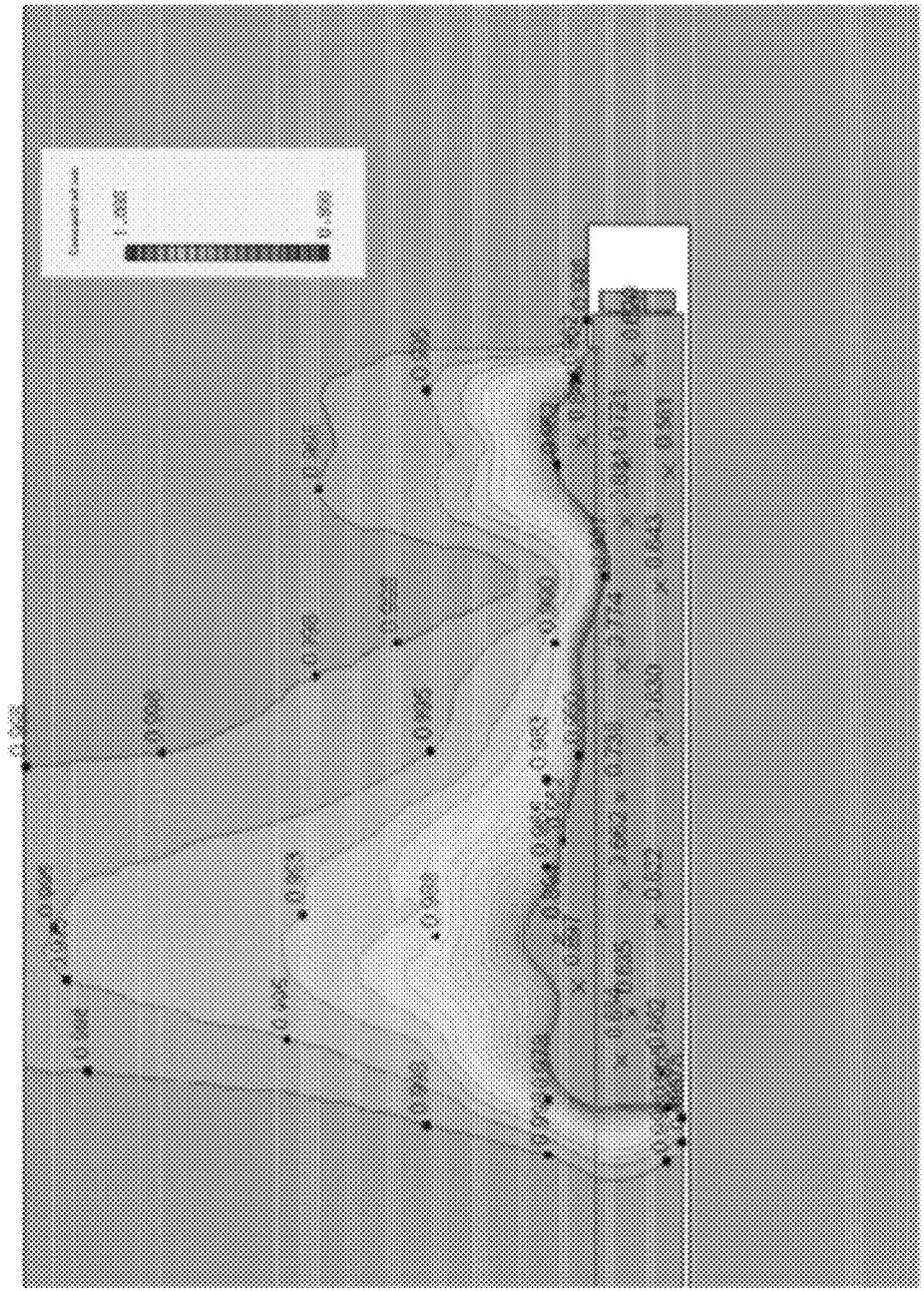

FIG. 5 is a transverse sectional view of the probe shown in FIG. 1. The tubular member 61 of the probe 60 is formed with the hole 67 on an upstream side near the end towards the flange 62. Accordingly, the sample gas S flows into the tubular member 61 through the hole 67 and forms a wall made of the sample gas S flow. As a result, purge air PA1 from the optical guiding tube 51 (not shown, right side of FIG. 5) toward the tubular member 61 is stopped from progressing further inward, i.e., toward the center of the measurement field 69 corresponding to the first part 61a of the tubular member 61, by the wall of the sample gas S flow. In addition, the tubular member 61 is formed with the hole 68 on the upstream side near the end toward the mirror 63. Accordingly, the sample gas S flows into the tubular member 61 through the hole 68 and forms a wall made of the sample gas S flow. As a result, purge air PA2 guided toward the mirror 63 through the purge air outflow tube 64 (see FIG. 1) is stopped from progressing further inward, i.e., toward the center of the measurement field 69 corresponding to the first part 61a of the tubular member 61, by the wall of the sample gas S flow.

As described above, in the probe 60, the wall of the sample gas S prevents the purge air PA (PA1 and PA2) from progressing further inward, so that it is possible to prevent the density of the sample gas S from being reduced in the measurement field 69 between the hole 67 and the hole 68, thereby allowing the measurement to be done accurately. In addition, since the hole 67 and the hole 68 are formed to define the effective cell length (i.e., the length of the measurement field 69), the measurement may be performed accurately based on the effective cell length and the attenuation amount of the measuring light. Furthermore, the hole formed on the upstream side near the end of the probe may be formed on both ends as in the probe 60, or may be formed only on one end.

FIG. 6 illustrates simulation results of the purge air blocking effect. FIG. 6A and FIG. 6B show simulation results when the hole 67 and the hole 68 are formed on the upstream side near the ends of the probe. FIG. 6A shows the immediate surroundings of the hole 67 (the surroundings of the pipe 96 wall surface), and FIG. 6B shows the immediate surroundings of the hole 68 (the center of the pipe 96). In contrast, FIG. 6C and FIG. 6D show simulation results when no holes are formed on the upstream side near the ends of the probe. FIG. 6C shows a portion of the probe corresponding to that shown in FIG. 6A and FIG. 6D shows a portion or the probe corresponding to that shown in FIG. 6B. In the figures, colorless (background) portions represent the same density as that of the sample gas S in the pipe 96, and colored (gray scale) portions represent a state in which the purge air and the sample gas S are mixed.

The settings for the simulation are as follows.
  Size of the hole 67 and the hole 68: 20 mm*20 mm (square);
  Diameter of the tubular member 61: 50 mm;
  Length between the hole 67 and the hole 68 (the length of the measurement field 69): 1000 mm;
  Flow velocity of the sample gas S: 15 m/second; and
  Temperature of the sample gas S: 450 degrees Celsius.
  Comparing FIG. 6A and FIG. 6B with FIG. 6C and FIG. 6D, in FIG. 6A and FIG. 6B, i.e. in the case where the hole 67 and hole 68 were formed, it is understood that the purge air was prevented from further flowing beyond the hole 67 and hole 68. According to the simulation results, in the case where the hole 67 and the hole 68 were formed (in FIG. 6A and FIG. 6B), the percentage of sample gas S within the measurement field 69 was 99.5%. In contrast, in the case where the hole 67 and hole 68 were not formed (in FIG. 6C and FIG. 6D), the percentage of sample gas S within the measurement field 69 was 82.1%.

2. Second Embodiment

The probe for gas analysis may be formed with small openings on the upstream side. Hereinafter, this embodiment will be explained.

Figure 7:
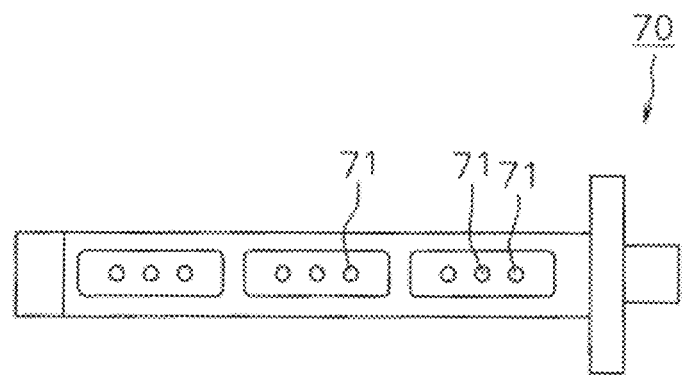
FIG. 7 is a plan view of a probe for gas analysis in another embodiment.

FIG. 7 is a plan view of a probe for gas analysis according to another embodiment. A probe for gas analysis 70 shown in FIG. 7 is formed with a plurality of small holes 71 on its upstream side. Between the plurality of small holes 71, predetermined gaps are formed. The probe 70 is formed with openings (not shown) along the effective cell length on the downstream side, similar to those in the probe 60 (see FIG. 2). The above-described openings on the downstream side will not be explained hereinafter because they have already been explained.

The diameter of the small holes 71 has a size such that the dust D flowing into the probe along with the sample gas S does not substantially affect the measurement. The diameter, the number, spaces or intervals, or the like of the small holes 71 may be adjusted so as to be within predetermined ranges, taking into consideration intensity of light emitted from the light source, the amount of dust in the sample gas S, or the like. More specifically, if the diameter of the tubular member 61 is 50 mm, and the length between the hole 67 and the hole 68 (the length of measurement field 69) is 1000 mm, the diameter of the small holes 71 may be 1 mm through 20 mm, and the space or intervals between the small holes 71 may be 10 mm through 50 mm. In another example, the diameter of the small holes 71 may be designed such that (A total area of the small openings)/(A contact area of the tubular member 61 with the sample gas S) may be 1/1000 through 1/10. It should be noted that "the contact area of the tubular member 61 with the sample gas S" means an area of the upstream portion in the entire surface of the tubular member, i.e., an area seen from the upstream side.

According to the probe 70, the small holes 71 are formed on the upstream side and the sample gas S flows into the probe 70 through the small holes 71, so that the dust is prevented from being deposited inside of the probe 70. Since the small holes 71 have a diameter such that the dust D flowing into the probe along with the sample gas S does not substantially affect the measurement, it is possible to ensure proper quantity of the measuring light passing through the inside of the probe.

3. Third Embodiment

The probe for gas analysis may be provided with a cover that opens and closes the openings formed on the downstream side along the effective cell length. Hereinafter, this example will be explained referring to FIG. 8 and FIG. 9.

Figures 8A, 8B:
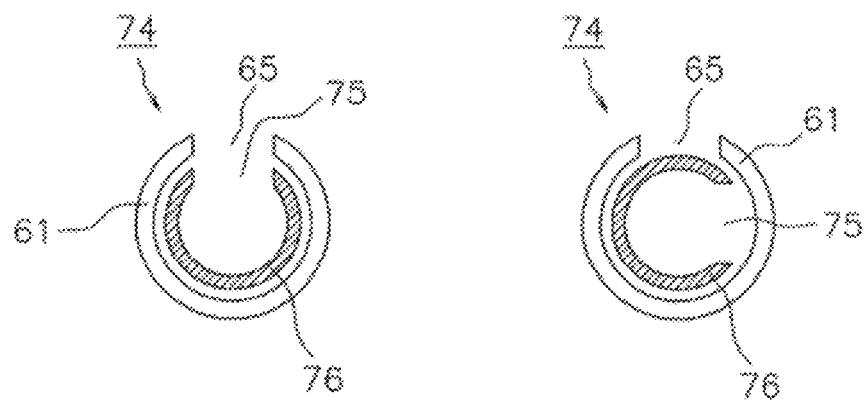
FIG. 8A and FIG. 8B are longitudinal sectional views of the probe for gas analysis in another embodiment.

FIG. 8A and FIG. 8B are longitudinal sectional views of a probe for gas analysis according to another embodiment. A probe for gas analysis 74 shown in FIG. 8A and FIG. 8B illustrates a structure in which a tubular member 76 is disposed within and in contact with the tubular member 61 of the probe 60 shown in FIG. 1, and the tubular member 76 is formed with openings 75 along an entire surface on one side. The tubular member 76 corresponds to the above-described cover. In an optical analyzer including the probe 74 as shown in FIG. 8A, when the openings 75 of the tubular member 76 and the openings 65 of the tubular member 61 form a positional relationship in which they are communicated with each other, the sample gas S is measured as is done in the optical analyzer 90.

On the other hand, when the tubular member 76 from a state of FIG. 8A is turned, the openings 75 of the tubular member 76 and the openings 65 of the tubular member 61 have a positional relationship n which there is no communication in between, as shown in FIG. 8B. In this state, the sample gas S cannot flow into the tubular member 61. Therefore, in this state, the tubular member 61 can be filled with a span gas so as to calibrate the measuring light. As described above, according to the probe 74, the tubular member 61 can be used for calibration as well as measurement, thereby simplifying the configuration of the probe for gas analysis. In addition, when the tubular member 76 is turned, the edges of the openings 75 of the tubular member 76 remove the dust adhered to the inner wall of the tubular member 61. The tubular member 76 may be turned manually by hand or by electrical power.

4. Fourth Embodiment

Figure 9A:
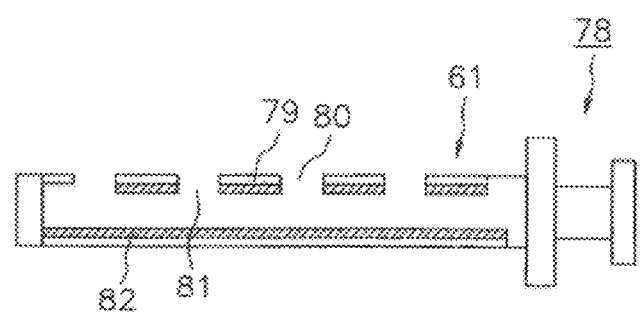
FIG. 9A and FIG. 9B are transverse sectional views of the probe for gas analysis in another embodiment.
Figure 9B:
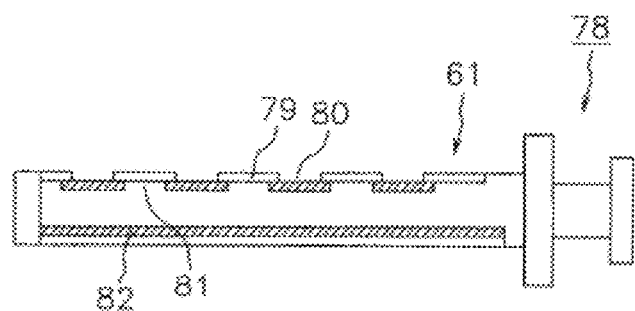
Figure 10:
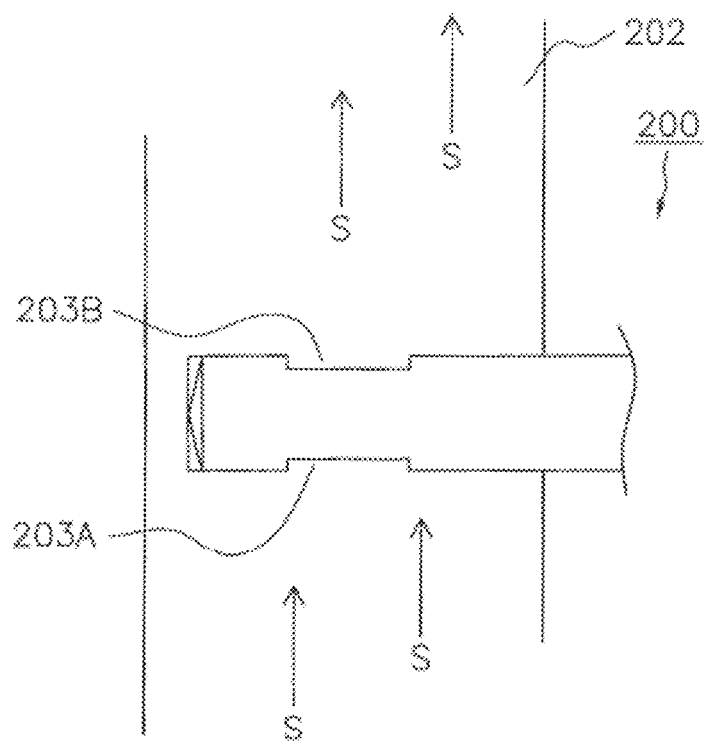
FIG. 10 is a side view illustrating a probe for gas analysis in the prior art.

FIG. 9A and FIG. 9B are transverse sectional views of a probe for gas analysis according to another embodiment. In a probe for gas analysis 78 shown in FIG. 9A and FIG. 9B, the tubular member 61 is formed with ribs 79 and openings 80 having the substantially same width. A tubular member 82 is provided within the tubular member 61. The tubular member 82 is in contact with the tubular member 61 from the inside, and is formed with a plurality of apertures 81 having the substantially same width as that of the openings 80. The apertures 81 are formed near the ribs 79 and the openings 80 of the tubular member 61. The tubular member 82 corresponds to the above-described cover. In the optical analyzer including the probe 78 as shown in FIG. 9A, when the apertures 81 of the tubular member 82 and the openings 80 of the tubular member 61 have a positional relationship in which there is communication in between, it is possible to analyze the sample gas S in a same way as in the above-described optical analyzer 90.

When the tubular member 82 from the state in FIG. 9A slides in a longitudinal direction (right-left direction in FIG. 9), the apertures 81 of the tubular member 82 and the openings 80 of the tubular member 61 have a positional relationship in which there is no communication in between, as shown in FIG. 9B. In this state, the sample gas S cannot flow into the tubular member 61. Accordingly, in this state, the tubular member 61 may be filled with a span gas so as to calibrate the measuring light. As described above, according to the probe 78, the tubular member 61 can be used for calibration as well as measurement, thereby simplifying the configuration of the probe for gas analysis. In addition, when the tubular member 82 slides in the longitudinal direction, the edges of the apertures 81 of the tubular member 82 remove the dust adhered to the inner wall of the tubular member 61. The tubular member 82 may be slid by hand or by electrical power.

5. Other Embodiments

The above-described embodiments can be combined with each other as appropriate. For example, the first embodiment can be carried out alone, and can also be combined with the third embodiment or the fourth embodiment. Further, the second embodiment can be carried out alone, and can also be combined with the third embodiment or the fourth embodiment.

According to the above-described embodiments, a case was explained in which the measuring light is introduced into the analysis unit 2 (probe for gas analysis 60) directly from the measuring device 10, but the measuring device and the analysis unit may be connected with each other through optical fibers or electrical wires, through which the measuring light is introduced into the analysis unit 2.

The measuring device 10 only has to measure objects to be analyzed using light, and is not limited to one type. For example, absorption spectrochemical methods such as TDLAS (Tunable Diode Laser Absorption Spectroscopy) can be used. When using TDLAS, the measuring device 10 can perform a gas concentration measurement of O2, CO, CO2, H2O, NH3, HCl, etc., having absorption spectrum between infrared region and near-infrared region based on a selection of measuring absorption waves. In addition, the measuring device 10 can perform a gas concentration measurement of SO2NO, NO2, etc., having absorption spectrum in the mid-infrared region, using a QCL (quantum-cascade laser) as a light source.

In the above-described embodiments, a case was explained in which the mirror 63 reflects the measuring light and the light detecting unit 12 located at the same position as the light source 11 detects the reflected light. However, a light detecting unit may be provided in place of the mirror 63 to detect the measuring light.

In the above-described embodiments, a case was explained in which the sample gas is analyzed for gas density. However, a thermometer may be employed based on TDLAS.

While only selected embodiments have been chosen to illustrate the present invention, it will be apparent to those skilled in the art from this disclosure that various changes and modifications can be made herein without departing from the scope of the invention defined in the appended claims. Furthermore, the foregoing descriptions of the embodiments are provided as examples only, and are not meant to limit the invention defined by the appended claims and their equivalents. Thus, the scope of the invention is not limited to the disclosed embodiments. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. Any embodiments described as less desirable than other embodiments or prior art implementations with respect to one or more characteristics are not outside the scope of the disclosure and may be desirable for particular applications. While the best mode has been described in detail, those familiar with the art will recognize various alternative designs and embodiments within the scope of the following claims.

What is claimed is:

1. A gas analysis probe for analyzing a sample gas flowing through a pipe, comprising:
   a tubular member having a measurement field and at least one sample gas inflow portion positioned so that sample gas flowing through the pipe flows around the tubular member through the at least one sample gas inflow portion to the measurement field; and
   the at least one sample gas inflow portion comprises apertures all of which are formed on a downstream side of the tubular member with respect to the direction of flow of the sample gas, wherein an upstream side of the tubular member corresponding to the measurement field is configured to prevent dust in the sample gas from entering the tubular member.

2. The gas analysis probe according to claim 1, wherein the apertures are positioned along an entire length of the measurement field.

3. The gas analysis probe according to claim 1, wherein
   the tubular member has elongate or linear shape with a symmetry axis along its extension defining a longitudinal direction, and the apertures are arranged in the longitudinal direction of the extension of the tubular member.

4. The gas analysis probe according to claim 1, wherein the tubular member has elongate or linear shape with a symmetry axis along its extension defining a longitudinal direction, and an opening angle of the aperture seen from a most downstream point in relation to the symmetry axis of the tubular member is less than about 90 degrees when the tubular member is seen in the longitudinal direction of its extension and divided along a circumferential direction.

5. The gas analysis probe according to claim 1, further comprising at least one purge air supplying unit configured to supply purge air into the tubular member while measuring the sample gas.

6. The gas analysis probe according to claim 5, wherein through at least one small hole, the sample gas flows into the tubular member to prevent the purge air from moving toward a center of the measurement field.

7. The gas analysis probe according to claim 6, wherein the at least one small hole having a diameter such that dust flowing into the tubular member along with the sample gas does substantially not affect measurement of the sample gas.

8. The gas analysis probe according to claim 1, further comprising a cover configured to open and close the apertures.

9. The gas analysis probe according to claim 8, wherein the cover is a tube-like member disposed within the tubular member and formed with second apertures respectively corresponding to the apertures, in particular with respect to at least one of its position, form and extension.

* * * * *